United States Patent [19]

Fujita et al.

[11] 4,377,526

[45] Mar. 22, 1983

[54] METHOD OF PURIFYING EICOSAPENTAENOIC ACID AND ITS ESTERS

[75] Inventors: Takao Fujita; Masahiro Makuta, both of Hachioji, Japan

[73] Assignee: Nippon Suisan Kaisha, Ltd., Tokyo, Japan

[21] Appl. No.: 329,883

[22] Filed: Dec. 11, 1981

[30] Foreign Application Priority Data

May 15, 1981 [JP] Japan .................................. 56-73168
Jul. 3, 1981 [JP] Japan ................................ 56-103207

[51] Int. Cl.$^3$ .............................................. B01D 3/34
[52] U.S. Cl. ............................ 260/424; 260/410.9 R; 260/419; 260/428.5
[58] Field of Search ..................... 260/398, 405, 405.5, 260/412, 412.1, 412.8, 413, 419, 420, 425, 426, 424, 410.9 R, 428.5; 203/39, 47, 48, 63, 66

[56] References Cited

U.S. PATENT DOCUMENTS 2,573,897 11/1951 Freeman et al. ................. 260/428.5

Primary Examiner—Frank Sever
Attorney, Agent, or Firm—Oblon, Fisher, Spivak, McClelland & Maier

[57] ABSTRACT

A method of purifying eicosapentaenoic acid and esters of eicosapentaenoic acid comprising subjecting a mixture containing eicosapentaenoic acid or an ester of eicosapentaenoic acid to the following steps in either order: (1) urea treatment, where the treatment comprises contacting the mixture with a polar organic solvent containing dissolved urea whereby a solution containing the acid or ester is formed, precipitating urea crystals from the solution, and removing the urea crystals, and (2) fractional distillation.

14 Claims, No Drawings

METHOD OF PURIFYING EICOSAPENTAENOIC ACID AND ITS ESTERS

BACKGROUND OF THE INVENTION

1. Field of the Invention

The present invention relates to a process for purifying eicosapentaenoic acid and its esters and more particularly to a process for purifying eicosapentaenoic acid and its esters to a high concentration on an industrial scale from natural fats and oils containing eicosapentaenoic acid or its derivatives.

2. Description of the Prior Art

It is known that eicosapentaenoic acid (which may hereinafter be referred to simply as "EPA") and its esters or amides are effective for medically treating or preventing certain thrombotic conditions such as myocardial or cerebral infarction (Japanese Laid-open Patent Application No. 15444/80).

Eicosapentaenoic acid is found in natural fats and oils, particularly in the fats and oils of marine animals such as the mackerel, sardine, or cod, either as itself or in the form of a derivative, such as a glyceride. Unfortunately, other fatty acids are always present in larger amounts. Although EPA is known to have the abovementioned medicinal effectiveness, it is still necessary for extensive basic studies, including clinical studies, to be conducted before EPA can be marketed as a medicine. For such studies, highly pure EPA is required in large amounts. However, prior to the present invention, there was no industrial method which was useful for separating EPA in a high concentration from natural fats and oils. This has been a bottleneck in the development of EPA as a medicine.

In order to concentrate a particular fatty acid from a mixture of various fatty acids or their esters, it has been common to use various methods such as dewaxing, counter current extraction, urea addition, distillation, liquid chromatography, and the like, depending upon the particular composition of the mixture of fatty acids available as the raw material. These methods have been used chiefly for the separation of relatively low molecular weight fatty acids from other fatty acids, or for the separation of saturated acids from unsaturated acids. The present situation is different from these previous separations. EPA is a highly unsaturated fatty acid having 20 carbon atoms and 5 double bonds. As is evident from its structure, it is quite unstable when exposed to oxygen, light, or heat. In fact, only with recent developments in the field of gas chromatography has the quantitative analysis of EPA become possible. Accordingly, it is difficult to readily and economically concentrate and separate EPA using the above-mentioned conventional methods.

Among the above-mentioned conventional methods, for instance, counter current extraction and liquid chromatography methods have been shown to be useful for the separation of EPA on a small scale. However, such methods require large amounts of various solvents and a long period of time. Accordingly, from the economic and practical points of view, they are totally unsatisfactory in industrial situations.

SUMMARY OF THE INVENTION

Accordingly, it is an object of this invention to provide a method of substantially purifying eicosapentaenoic acid and its esters without degradation.

It is a further object of this invention to provide a method of substantially purifying eicosapentaenoic acid and its esters on an industrial scale.

These and other objects of the invention as will hereinafter become more readily apparent have been accomplished by providing a method of purifying eicosapentaenoic acid and esters of eicosapentaenoic acid comprising subjecting a mixture containing eicosapentaenoic acid or an ester of eicosapentaenoic acid to the following steps in either order: urea treatment, wherein said treatment comprises contacting said mixture with a polar organic solvent containing dissolved urea whereby a solution containing said acid or ester is formed, precipitating urea crystals from said solution, and removing said crystals from said solution; and fractional distillation.

DETAILED DESCRIPTION OF THE PREFERRED EMBODIMENTS

The present inventors have conducted a study with a goal of obtaining EPA or its esters from natural fats and oils in an industrially advantageous manner, and have found that it is possible to advantageously concentrate eicosapentaenoic acid or its esters from a fatty acid mixture obtained from a natural fat or oil containing eicosapentaenoic acid or its derivatives by a combination of urea treatment and distillation.

Natural fats or oils containing high levels of EPA suitable for use in the present invention include, for example, fats and oils of blue-colored fish such as the mackerel, sardine, mackerel pike and herring; cod-liver oil; and animal marine planktons, such as krill and the various shrimp-like copepods known in Japanese as "okiami". Among these, fats and oils of krill, sardines, mackerel pikes, herrings, or mackerels are useful, among others, as the raw material for the second embodiment of the invention as they contain lesser amounts of highly unsaturated fatty acids having molecular weights close to the molecular weight of EPA.

In the present invention, the natural fat or oil is subjected to saponification or alcoholysis according to usual methods thereby to convert triglycerides to free fatty acids or esters of fatty acids having low boiling points (both of these will be generally referred to as "fatty acid mixtures"). If esters are formed by alcoholysis, preferred are alkyl esters containing 1- to 5-carbon alkyl groups with ethyl esters being most preferred.

Natural fats and oils usually contain, as their constituent fatty acids, saturated fatty acids having melting points lower than EPA and fatty acids having a lower degree of unsaturation (hereinafter referred to collectively as "low unsaturated fatty acids") such as $C_{14:0}$, $C_{16:0}$, $C_{16:1}$, $C_{18:0}$, $C_{18:1}$, $C_{20:0}$, or $C_{10:1}$, in an average amount of 60%. The representation $C_{x:y}$ here and elsewhere refers to a fatty acid having x carbon atoms and y double bonds.

Accordingly, if natural fats and oils are subjected to distillation, it takes a long period of time to distill off the above-mentioned low unsaturated fatty acids as the initial distillate fraction, thus leading to thermal degradation of EPA.

The present inventor have found that in a first embodiment of the invention it is possible to advantageously obtain EPA or its ester by first subjecting the fatty acid mixture to a urea treatment to remove the low unsaturated fatty acids and then subjecting the remaining material to distillation. In the urea treatment, urea is added to a polar organic solvent capable of readily dissolving urea therein, such as methanol or ethanol, and dissolved therein, if necessary with heating, to obtain a urea solution which normally contains from 10 to 20% of urea. To this solution, the fatty acid mixture is added and stirred. The amount of urea in the solution is adjusted to be at least 0.5 part by weight, preferably from 1 to 2 parts, relative to one part by weight of the fatty acid mixture. The urea solution is mixed homogeneously with the fatty acid mixture.

Then the urea is precipitated, preferably by cooling the urea-treated solution. At this time, low unsaturated fatty acids in the fatty acid mixture will be attached to the precipitated urea crystals to form a complex which can be separated. The cooling may be conducted by leaving the solution to stand for a long period of time if desired. However, from the standpoint of efficiency of the operation, it is desirable to forceably cool the solution, for example with use of water. Good results will be obtained when the solution is cooled to a temperature of at most 50° C., preferably from 30° to 40° C.

The urea crystals thus obtained (to which low unsaturated fatty acids are attached) are then filtered off or otherwise removed. The solution obtained is concentrated to remove the major portion of the solvent, and then water and a non-polar solvent such as n-hexane are added, whereupon the remaining urea is extracted into the aqueous layer and fatty acids having a high degree of unsaturation (hereinafter referred to as "highly unsaturated fatty acids") are extracted into the solvent layer. The aqueous layer and the organic solvent layer separate on standing with the aqueous layer generally constituting the lower layer. The aqueous layer is discarded, and the upper solvent layer is washed with water. If distillation is carried out while even a small amount of urea remains, the color of the EPA-containing solution changes to brown, the distillate fraction will be colored, and the rate of distillation is considerably slowed down. Consequently, separation of EPA requires a high temperature and a long period of time if urea remains, and EPA undergoes degradation. Therefore, it is an essential requirement to remove the remaining urea completely. The removal of the last traces of the remaining urea can be accomplished, for instance, by washing the solvent layer with an aqueous dilute acid solution, or by adsorption of urea using an adsorbent such as silicic acid, activated clay, activated alumina or activated carbon, either in a batch system or a continuous column system. The solvent layer thus treated can be tested with ninhydrin to ensure that no urea is present, and then subjected to the subsequent distillation step, whereby the EPA-containing solution can be distilled without any trouble.

By initially distilling off the solvent from the solvent layer from which the last trace of urea has been removed, a residue fraction containing highly unsaturated fatty acids as the major component is obtained.

Then, the highly unsaturated fatty acids are subjected to fractional distillation. Since most of the low saturated fatty acids contained in the natural fat or oil are removed by the urea treatment, little time is required to cut the initial distillate fraction prior to EPA reaching the still head, and it is possible to fractionate the main distillation fraction, containing the desired EPA in a high concentration, in a short period of time without degrading the EPA.

The distillation apparatus to be used for the fractionation may be any one of a plate tower type, a bubble cap tower type, a packed tower type, and the like. The method of distillation may be a batch system or a continuous system, and it may, for example, be carried out in the following manner. Namely, the number of theoretical plates of the fractioning tower is at least 2 plates, preferably from 3 to 10 plates; the distillation is carried out under vacuum conditions with a pressure of at most 5 mmHg, preferably at most 1 mmHg; the heating temperature is at most 250° C., preferably at most 210° C.; the retention time until the completion of the fractionation of the main distillate fraction is less than 4 hours, preferably less than 3 hours; and the distillation is preferably carried out under circulation of an inert gas such as nitrogen.

The EPA thus obtained can be, if necessary, treated to remove any trace of impurities, for example by column adsorption. Further, in the case where low unsaturated fatty acids remain which were not completely removed by the first urea treatment, it is possible to increase the concentration of EPA by subjecting it to further urea treatment, or the purity may be increased by a conventional refining method. Even in the latter cases, the refining operation can readily be accomplished without degradation as the EPA concentration has already been adequately increased by the process of the present invention.

Thus, the first embodiment of the invention is a process for producing eicosapentaenoic acid or its ester which comprises treating a fatty acid mixture obtained from a natural fat or oil containing eicosapentaenoic acid or a derivative of eicosapentaenoic acid with urea to remove low unsaturated fatty acids to give a partially purified mixture and then fractionally distilling the purified mixture to obtain eicosapentaenoic acid.

According to the first embodiment of the invention, since most of the low unsaturated fatty acids are removed by the urea treatment, little time is required to cut the initial distillate fraction prior to fractionation of EPA by distillation. Thus, the main distillate fraction containing the desired EPA in a high concentration is thereby obtainable without degradation. On the other hand, since the raw material of the fatty acid mixture is directly subjected to the urea treatment, about 1.5 times as much urea is used as raw material and about 10 times as much alcohol. Consequently, there are disadvantages that the apparatus used must be large, the operation thereof is complicated, and regeneration treatment of the abundant wastes formed by the process is difficult. Nevertheless, the process provides pure EPA in good yield at a reasonable cost.

In order to overcome some of the disadvantages of the first embodiment, the present inventor have conducted further research and have found that conventional distillation of the fatty acid mixture inevitably requires a long period of time for the removal of the initial distillate fraction, particularly for batch distillation, if distillation is carried out as the first step of the purification process. Under such circumstances, it is possible to avoid degradation of EPA as the retention time of EPA under heating is too long. Nevertheless, it is possible to obtain EPA or its ester in a high concentration by first collecting the main distillate fraction containing EPA or its ester by means of a distillation apparatus in which distillation can be conducted continuously within a short period of time, even though this first step results in only partial purification, and then subjecting the main distillate fraction to urea treatment. However, if this second embodiment of the invention is carried out using a fatty acid mixture containing a large amount of highly unsaturated fatty acids having molecular weights close to the molecular weight of the EPA, it is impossible to remove the highly unsaturated fatty acids even by the subsequent urea treatment. Accordingly, in such cases it is impossible to increase the concentration of EPA to the desired levels. Nevertheless, this process is advantageous for the treatment of a natural fat or oil which contains a relatively low amount of highly unsaturated fatty acids having molecular weights close to the molecular weight of the EPA.

Thus, the second embodiment of the invention is a process for purifying eicosapentaenoic acid or its ester, which comprises continuously distilling a fatty acid mixture obtained from a natural fat or oil containing eicosapentaenoic acid or a derivative of eicosapentaenoic acid to obtain a main distillate fraction containing at least 40% by weight of eicosapentaenoic acid or its ester, and then subjecting the main distillate fraction to urea treatment.

In the practice of the second embodiment invention, the fatty acid mixture is first subjected to distillation. The distillation must be such that the retention time under heating is short, and because of this requirement, a continuous distillation method is employed. For the continuous distillation, a conventional continuous distillation apparatus may be used, but it is preferred to use a conbination of two fractionating towers of the packed column type or spring type having from 3 to 5 theoretical plates, whereby one fractionating tower is used for removal of the initial distillate fraction and the other fractionating tower is used for collecting the main distillate fraction.

The distillation is carried out under vacuum at a pressure of at most 5 mmHg, preferably at most 1 mmHg. For instance, if the vacuum pressure is set to be about 1 mmHg, the removal of the initial distillate fraction can be carried out at a temperature of from 180° to 200° C. for from 40 to 60 minutes. Then, a fraction distilled at a temperature of from 200° to 210° C. under the same vacuum pressure is collected as the main distillate fraction. The collection of the main distillate fraction is completed in from 40 to 60 minutes. For this distillation, it is preferred that the retention time be as short as possible. For this purpose, it is preferred that a fraction having a wide range of boiling points be collected as the main distillate fraction. However, if the width of the main distillate fraction is too great, the EPA concentration becomes low and EPA of a high concentration can not be obtained even when subjected to the subsequent urea treatment. Therefore, it is desireable to collect a main distillate fraction containing at least 40% by weight, preferably from 40 to 60% by weight of EPA or its ester. (Hereinafter, "% by weight" will be represented simply by "%".) Afterwards, the main distillate fraction thus obtained is subjected to urea treatment. The urea treatment is carried out in the same manner as in the first embodiment of the invention discussed above.

As mentioned above, according to the present embodiment, an apparatus of a large scale is not required, and it is possible to produce the EPA or its ester in a simple operation and in a high concentration at a level of at least 70%. Thus, the processes of the present invention are extremely useful as industrial processes.

The above disclosure generally describes the present invention. A more complete understanding can be obtained by reference to the following specific examples which are provided herein for purposes of illustration only and are not intended to be limiting unless otherwise specified.

EXAMPLE 1

(i) Immediately after preparation, 0.1% of tocopherol was added to a fish oil prepared from pollacks (as the major raw material) aboard a North Pacific bottom-fish factory ship. The fish oil was immediately frozen at −28° C. and transported to Japan (this fish oil will hereinafter be referred to as "factory ship fish oil").

Ethanol (30 kg) containing 1 kg of sodium ethoxide dissolved therein was added to 100 kg of the factory ship fish oil, and the mixture was stirred. The esterification reaction was carried out at 20° C. for 6 hours. The reaction solution was then allowed to stand, and the glycerin which separated was removed. The reaction was stopped by adding water. Washing was carried out using 150 l of warm water (about 40° C.) until the water after washing became neutral. Then, continuous centrifugal separation was carried out at 10,000 G for 10 minutes to remove water, whereupon 85 kg of a mixture of ethyl esters of fatty acids was obtained. The results obtained by the gas chromatographic analysis of the fatty acid composition of the mixture are shown in Table 1(a).

(ii) With the use of a reaction tank equipped with a steam heating coil and a water cooling jacket and having a capacity of 1.5 t, 128 kg of urea were dissolved in 680 l of ethanol heated to a temperature of 70° C., and 85 kg of the mixture of ethyl esters of fatty acids obtained by step (i) were added and stirred at 70° C. for 10 minutes. Afterwards, the reaction solution was cooled to a temperature of 35° C., whereupon a complex comprising urea and ethyl esters of low unsaturated fatty acids was precipitated. The precipitated crystals were filtered off, and the filtrate was concentrated under reduced pressure, thereby removing the major portion of ethanol. Water (425 l) and n-hexane (425 l) were added, whereupon urea was extracted into the n-hexane layer. After allowing the mixture to separate on standing, the lower aqueous layer was discarded, and the n-hexane layer was washed 5 times with 850 l of warm water (40° C.). After removing water from the n-hexane layer, the n-hexane layer was passed through a silicic acid column having an inner diameter of 10 cm and a height of 27 cm at a rate of 80 cm/H to remove by adsorption the remaining trace of urea. The solution eluted from the column was concentrated under reduced pressure to distill off the n-hexane, whereupon 42.5 kg of a mixture of urea-treated ethyl esters of fatty acids was obtained. According to the gas chromatographic analysis, the fatty acid composition of the mixture was as shown in Table 1(b).

(iii) The urea-treated ethyl esters of fatty acids (42.5 kg) were fed at a rate of 14 l/H to a fractionating tower having 10 theoretical plates, whereby 8.9 kg (21%) of the initial distillate fraction was cut, and 24.2 kg (57%) of the main distillate fraction was obtained. The retention time of the main distillate fraction was 90 minutes, and the temperature of the ethyl esters fed to the distillation vessel at the end of the fractionation of the main distillate fraction was 203° C. The results of gas chromatographic analysis of the fatty acid composition of the product thus obtained are as shown in Table 1(c).

TABLE 1

| Fatty acids | Raw material of a mixture of fatty acids (a) | Urea-treated products (b) | Products of the present invention (c) |
|---|---|---|---|
| 12-0 | 0.03 | | |
| 14-0 | 5.9 | 0.4 | |
| 14-1 | 0.01 | 0.008 | |
| 15-0 | 0.26 | | |
| 15-1 | 0.3 | 1.5 | |
| 16-0 | 12.4 | | |
| 16-1 | 10.9 | 4.8 | |
| 17-0 | 0.3 | | |
| 17-1 | 0.8 | 1.4 | |
| 18-0 | 2.7 | | |
| 18-1 | 16.8 | 1.2 | |
| 18-2 | 1.9 | 5.6 | 1.0 |
| 18-3 | 0.05 | 0.04 | |
| 18-4 | 1.7 | 6.1 | 1.5 |
| 19-0 | | | |
| 19-1 | 0.3 | | |
| 20-1 | 14.7 | 0.09 | |
| 20-2 | 0.08 | | |
| 20-3 | | | |
| 20-4 | | | |
| 20-5 | 14.5 | 57.3 | 92.9 |
| 21-1 | | | |
| 22-1 | 10.8 | 0.06 | 0.01 |
| 22-2 | | | |
| 22-3 | | | |
| 22-4 | | | |
| 22-5 | 1.0 | 3.8 | 2.5 |
| 22-6 | 4.3 | 17.5 | 2.0 |
| 23-1 | | | |
| 24-1 | 0.4 | 1.5 | 0.09 |
| 24-4 | | | |

Note:
The values in the Table are by %, and blanks represent 0%. The abbreviations, 12-0, etc., under the heading "Fatty Acids" represent the number of carbon atoms and double bonds of a particular fatty acid. For example, 20-5 is eicosapentaenoic acid.

EXAMPLE 2

A phosphoric acid buffer solution (200 ml, pH 7.5) was added to 100 kg of an oil extracted from dried krill with n-hexane. The mixture was vigorously stirred at 40° C. and then hydrolyzed using a lipase agent, whereupon 61 kg of a mixture of free fatty acids was obtained. According to gas chromatographic analysis, the fatty acid composition of this mixture was as shown in Table 2(a).

The entire fatty acid mixture thus obtained was treated with urea in the same manner as in Example 1, and highly unsaturated fatty acids to which no urea was attached were obtained in the n-hexane layer. The n-hexane layer was washed 3 times with 300 l of water. After removing water, 1 kg of active alumina and 1 kg of active carbon were added to the n-hexane layer and stirred for 20 minutes, the adsorbents were filtered off, and the filtrate was concentrated under reduced pressure to remove n-hexane, whereupon 30 kg of highly unsaturated fatty acids were obtained. According to gas chromatographic analysis, the fatty acid composition of this mixture was as shown in Table 2(b).

Then, 30 kg of this fatty acid mixture was distilled by a fractionating tower packed with McMahon packing and having 5 theoretical plates, whereby 8 kg (26.8%) of the initial distillate fraction was cut and then 12.3 kg (41%) of the main distillate fraction was obtained. The vacuum pressure at this time was at most 1 mmHg at the top of the tower, and 2.5 mmHg at the still. The temperature at the end of fractionation of the main distillate fraction was 209° C., and the retention time was 3.5 hours. According to chromatographic analysis, the fatty acid composition of this mixture was as shown in Table 2(c).

TABLE 2

| Fatty acids | Raw material of a mixture of fatty acids (a) | Urea-treated products (b) | Products of the present invention (c) |
|---|---|---|---|
| 12-0 | 0.3 | | |
| 14-0 | 11.2 | 0.5 | |
| 14-1 | 0.3 | 0.2 | |
| 15-0 | 0.9 | | |
| 15-1 | | | |
| 16-0 | 17.8 | | |
| 16-1 | 6.2 | 1.7 | |
| 16-2 | 1.7 | 3.0 | |
| 17-0 | 0.1 | | |
| 17-1 | 0.9 | 0.9 | |
| 18-0 | 1.2 | | |
| 18-1 | 14.7 | 0.6 | |
| 18-2 | 3.4 | 6.1 | |
| 18-3 | 1.5 | 0.7 | |
| 18-4 | 3.1 | 6.7 | 1.0 |
| 19-0 | 0.4 | | |
| 19-1 | 0.1 | | |
| 20-0 | 0.3 | | |
| 20-1 | 0.1 | | |
| 20-2 | 0.1 | | |
| 20-3 | 1.4 | 0.6 | |
| 20-4 | 0.6 | 1.3 | |
| 20-5 | 17.3 | 40.9 | 89.5 |
| 21-1 | 0.3 | | |
| 22-1 | 0.3 | | |
| 22-2 | 0.2 | 3.7 | 5.0 |
| 22-3 | 2.4 | 1.1 | 1.2 |
| 22-4 | 0.4 | 0.8 | 0.5 |
| 22-5 | 0.4 | 0.9 | 0.3 |
| 22-6 | 11.1 | 27.0 | 2.0 |
| 23-1 | 0.2 | | |
| 24-1 | | | |
| 24-4 | 1.1 | 2.3 | 0.5 |

EXAMPLE 3

Under the same conditions as in Example 1, 100 kg of a mackerel oil was ethyl esterified, then treated with urea, and fractionally distilled, whereupon 8 kg of a main distillate fraction was obtained.

Further, 8 kg of the main distillate fraction was treated with urea (65 l of ethanol containing 12 kg of urea) in accordance with section (ii) of Example 1, whereupon 4.5 kg of highly unsaturated fatty acids were obtained. According to gas chromatographic analysis, the fatty acid composition thereof was as shown in Table 3(b).

TABLE 3

| Fatty acids | Raw material of a mixture of fatty acids (a) | Products of the present invention (b) |
|---|---|---|
| 12-0 | 0.1 | |
| 14-0 | 4.9 | |
| 14-1 | 0.4 | |
| 15-0 | 0.6 | |
| 15-1 | 0.2 | |
| 16-0 | 17.7 | |
| 16-1 | 5.5 | |
| 17-0 | 1.4 | |
| 17-1 | 0.9 | |
| 18-0 | 4.0 | |
| 18-1 | 23.7 | |
| 18-2 | 2.0 | |
| 18-3 | 0.1 | |
| 18-4 | 2.2 | 1.3 |
| 19-0 | | |
| 19-1 | | |
| 20-1 | 8.2 | |

TABLE 3-continued

| Fatty acids | Raw material of a mixture of fatty acids (a) | Products of the present invention (b) |
|---|---|---|
| 20-2 | | |
| 20-3 | | |
| 20-4 | 0.6 | 3.1 |
| 20-5 | 8.7 | 89.9 |
| 21-1 | | |
| 22-1 | 7.6 | 0.8 |
| 22-2 | | |
| 22-3 | | |
| 22-4 | 0.1 | |
| 22-5 | 1.4 | 1.5 |
| 22-6 | 8.1 | 3.3 |
| 23-1 | | |
| 24-1 | 1.6 | |
| 24-4 | | |

EXAMPLE 4

(i) A sardine oil was subjected to alcoholysis in the presence of sodium ethoxide as the catalyst according to usual methods, whereupon a mixture of ethyl esters of fatty acids was obtained. This mixture was analyzed by gas chromatography for the composition of the major fatty acids, and the results obtained are shown in Table 4(a).

(ii) This fatty acid mixture (84 l) was fed to a first tower of a double-tower, packing-type, continuous distillation apparatus at a rate of 14 l/H, 49.6 l (59%) of the initial distillate fraction was continuously cut, and the remainder was continuously fed to the second tower, whereupon 24 l (28.5%) of the main distillate fraction was fractionated. The number of theoretical plates of the first tower was 5 plates, the packing material was half rings, the temperature at the top of the tower was 195° C., and the retention time was 45 minutes. The number of theoretical plates of the second tower was 5 plates, the packing material was spring coils, the temperature at the top of the tower was 208° C., and the retention time was 55 minutes. According to gas chromatographic analysis, the fatty acid composition of the fractionated main distillate fraction was as shown in Table 4(b).

(iii) Then, in a reaction tank, 128 g of urea was dissolved in 680 l of ethanol heated to a temperature of 70° C., and 84 kg of the main distillate fraction obtained by (ii) was added with stirring to obtain a homogeneous mixture. Upon cooling to 37° C., a complex of urea and ethyl esters of low unsaturated fatty acids precipitated. The precipitate crystals were filtered off, and the filtrate was concentrated under reduced pressure to remove the major portion of ethanol. Then, 425 l of water and 425 l of n-hexane were added, whereupon urea was extracted into the aqueous layer and the ethyl esters were extracted into the n-hexane layer. After standing to allow separation, the lower aqueous layer was discarded, and the n-hexane layer was washed 5 times with 850 l of warm water (40° C.). After removing water, the hexane layer was refined by passing it through a silicic acid column having an inner diameter of 10 cm and a height of 27 cm at a rate of 80 cm/H. The solution eluted from the column was concentrated under reduced pressure to remove n-hexane, whereupon 55 kg of ethyl esters of fatty acids of the present invention were obtained. The results obtained by analysis of the fatty acid composition of the products thus obtained by gas chromatography are shown in Table 4(c).

TABLE 4

| Fatty acids | Raw material of a mixture of ethyl esters of fatty acids (a) | Distillation treated products (b) | Products of the present invention (c) |
|---|---|---|---|
| 14-0 | 8.1 | 0 | 0 |
| 14-1 | 0.3 | 0 | 0 |
| 16-0 | 18.4 | 2.1 | 0 |
| 16-1 | 9.7 | 0.8 | 0 |
| 17-0 | 1.1 | 0.5 | 0 |
| 17-1 | 1.4 | 0.3 | 0 |
| 18-0 | 4.7 | 6.6 | 0 |
| 18-1 | 13.2 | 20.3 | 0 |
| 18-2 | 3.7 | 2.3 | 1.4 |
| 18-3 | 1.0 | 2.3 | 1.7 |
| 18-4 | 2.1 | 3.0 | 4.2 |
| 19-1 | 0.3 | 0.9 | 0.4 |
| 20-1 | 2.2 | 5.7 | 0.1 |
| 20-2 | 0.5 | 1.8 | 2.0 |
| 20-3 | 0.1 | 0.4 | 0.5 |
| 20-4 | 1.9 | 2.1 | 2.8 |
| 20-5 | 17.6 | 43.2 | 74.4 |
| 22-1 | 1.3 | 3.6 | 5.9 |
| 22-4 | 0.7 | 0 | 0 |
| 22-5 | 2.5 | 0.6 | 1.4 |
| 22-6 | 7.7 | 2.2 | 5.0 |
| 24-1 | 0.8 | 0.9 | 0.2 |

EXAMPLE 5

(i) An oil extracted from dried fish with n-hexane was saponified by usual methods, whereby a fatty acid mixture was obtained. According to gas chromatographic analysis, the fatty acid composition of this mixture was as shown in Table 5(a).

(ii) This fatty acid mixture (59 l) was distilled by the apparatus of Example 4 part (ii), whereby 34.2 l (58%) of the initial distillate fraction was cut and 9.5 l of the main distillate fraction was collected. According to gas chromatography analysis, the fatty acid composition of this mixture was as shown in Table 5(b).

(iii) Then, several main distillate fractions obtained by the procedure of part (ii) were pooled to give a 100 kg sample. In a manner similar to Example 4, urea treatment and silicic acid column refining were carried out on this sample. After removal of solvent, 63 kg of the fatty acids of the present invention were obtained. The fatty acid composition of the mixture thus obtained was analyzed by gas chromatography, and the results thereby obtained are shown in Table 5(c).

TABLE 5

| Fatty acids | Raw material of a mixture of ethyl esters of fatty acids (a) | Distillation treated products (b) | Products of the present invention (c) |
|---|---|---|---|
| 12-0 | 0.1 | 0 | 0 |
| 13-0 | 0.1 | 0 | 0 |
| 13-1 | 0.1 | 0 | 0 |
| 14-0 | 5.3 | 0 | 0 |
| 14-1 | 0.9 | 0 | 0 |
| 15-0 | 1.1 | 0 | 0 |
| 15-1 | 0.5 | 0 | 0 |
| 16-0 | 19.3 | 2.5 | 0 |
| 16-1 | 5.0 | 0.5 | 0 |
| 17-0 | 2.1 | 1.0 | 0 |
| 17-1 | 1.5 | 0.4 | 0 |
| 18-0 | 1.4 | 2.5 | 0 |
| 18-1 | 15.0 | 25.0 | 0 |
| 18-2 | 3.5 | 3.1 | 2.6 |
| 18-3 | 1.7 | 3.3 | 1.4 |
| 18-4 | 2.1 | 3.0 | 4.2 |
| 19-1 | 1.0 | 3.2 | 0.5 |
| 20-0 | 0.2 | 0.4 | 0 |

TABLE 5-continued

| Fatty acids | Raw material of a mixture of ethyl esters of fatty acids (a) | Distillation treated products (b) | Products of the present invention (c) |
|---|---|---|---|
| 20-1 | 0.9 | 1.8 | 0.6 |
| 20-2 | 0.3 | 1.1 | 3.3 |
| 20-4 | 2.5 | 2.4 | 4.1 |
| 20-5 | 16.6 | 48.8 | 79.6 |
| 22-1 | 0.1 | 0.3 | 0 |
| 22-6 | 18.4 | 0.7 | 3.7 |

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method of purifying eicosapentaenoic acid and esters of eicosapentaenoic acid, comprising:
   treating a mixture containing eicosapentaenoic acid or an ester of eicosapentaenoic acid with urea, wherein said treating comprises contacting said mixture with a polar organic solvent and urea so that a solution containing said acid or ester and urea is formed, precipitating urea crystals from said solution, and removing said crystals from said solution; and
   fractionally distilling said mixture.

2. The method of claim 1, wherein said distilling comprises heating at no more than 250° C. for no more than 4 hours.

3. The method of claim 1, wherein said solvent is ethanol or methanol.

4. The method of claim 1, wherein urea is present in said solution at a concentration of 10 to 20% by weight.

5. The method of claim 1, wherein the weight ratio of urea to said acid or ester is at least 0.5.

6. The method of claim 5, wherein said ratio ranges from 1 to 2.

7. The method of claim 1, wherein said mixture is a natural fat or oil.

8. The method of claim 1, wherein said mixture is obtained by saponification or alcoholysis of a natural fat or oil.

9. The method of claim 7 or 8, wherein said natural fat or oil is obtained from a marine organism.

10. The method of claim 1, wherein said ester is a lower alkyl ester having 1 to 5 carbon atoms in the alkyl portion thereof.

11. The method of claim 10 wherein said ester is an ethyl ester.

12. The method of claim 1, wherein said urea treating preceeds said fractionally distilling.

13. The method of claim 1, wherein said fractionally distilling comprises continuous distilling wherein a main distillate fraction containing at least 40% by weight of said acid or said ester is obtained, and wherein said fractionally distilling preceeds said treating with urea.

14. The method of claim 13, wherein said main distillate fraction is obtained within no more than two hours.

* * * * *